(12) United States Patent
Sasaki

(10) Patent No.: US 11,526,982 B2
(45) Date of Patent: Dec. 13, 2022

(54) IMAGE PROCESSING DEVICE, IMAGE PROCESSING METHOD, AND PROGRAM

(71) Applicant: CANON KABUSHIKI KAISHA, Tokyo (JP)

(72) Inventor: Shoya Sasaki, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 347 days.

(21) Appl. No.: 16/828,759

(22) Filed: Mar. 24, 2020

(65) Prior Publication Data
US 2020/0311921 A1 Oct. 1, 2020

(30) Foreign Application Priority Data
Mar. 28, 2019 (JP) .............................. JP2019-064694

(51) Int. Cl.
| | |
|---|---|
| *G06K 9/00* | (2022.01) |
| *G01D 7/00* | (2006.01) |
| *G06T 7/00* | (2017.01) |
| *G06T 7/90* | (2017.01) |
| *H04N 1/60* | (2006.01) |
| *A61B 5/00* | (2006.01) |

(52) U.S. Cl.
CPC .......... *G06T 7/0012* (2013.01); *A61B 5/0095* (2013.01); *A61B 5/742* (2013.01); *G06T 7/90* (2017.01); *H04N 1/6002* (2013.01); *A61B 5/4312* (2013.01); *G06T 2200/24* (2013.01); *G06T 2207/30101* (2013.01)

(58) Field of Classification Search
CPC ......... G06K 9/00; G01N 21/1702; G01D 7/00
USPC ....... 382/100, 103, 106, 128–132, 154, 162, 382/172, 173, 181, 199, 214, 219, 254, 382/260, 274, 286–291, 305, 321, 167; 73/587
See application file for complete search history.

(56) References Cited

U.S. PATENT DOCUMENTS

| | | | |
|---|---|---|---|
| 9,854,187 B2* | 12/2017 | Naruse | G06T 5/20 |
| 10,049,438 B2* | 8/2018 | Naruse | H04N 5/361 |
| 2011/0239766 A1* | 10/2011 | Nakajima | G01N 21/1702 73/587 |
| 2017/0055844 A1* | 3/2017 | Umezawa | A61B 5/0091 |
| 2017/0168150 A1* | 6/2017 | Fukutani | A61B 5/0035 |
| 2017/0193642 A1* | 7/2017 | Naruse | G06T 5/001 |

OTHER PUBLICATIONS

L. V. Wang, et al. "Photoacoustic Tomography: In Vivo Imaging from Organelles to Organs", Science, vol. 335 (Mar. 2012).

\* cited by examiner

*Primary Examiner* — Seyed H Azarian
(74) *Attorney, Agent, or Firm* — Canon U.S.A., Inc. IP Division

(57) ABSTRACT

An image processing device disclosed in the present specification includes a display control unit configured to display, on a display unit, an image obtained by visualizing functional information related to optical characteristics of a subject based on a photoacoustic signal obtained by receiving a photoacoustic wave generated in the subject by irradiating the subject with light, and a correction unit configured to correct the functional information of the image displayed on the display unit based on a first image value of the functional information of the image displayed on the display unit and a second image value of the functional information.

16 Claims, 8 Drawing Sheets

IMAGE PROCESSING DEVICE, IMAGE PROCESSING METHOD, AND PROGRAM

BACKGROUND

Field of the Disclosure

The disclosure of the present specification relates to an image processing device, an image processing method, and a program.

Description of the Related Art

Photoacoustic imaging is known that irradiates a subject such as a living body with pulse light and displays a photoacoustic image indicating information inside the subject based on an acoustic wave (also called photoacoustic wave) generated by a photoacoustic effect.

In the photoacoustic imaging, it is possible to generate a photoacoustic image representing a spatial distribution of a sound pressure (initial sound pressure) of an acoustic wave generated by optical absorption, an optical absorption coefficient, or the like.

In addition, in the photoacoustic imaging, it is also possible to generate new image data indicating functional information by using a plurality of photoacoustic images obtained by a photoacoustic device.

L. V. Wang, et al. "Photoacoustic Tomography: In Vivo Imaging from Organelles to Organs" Science, Vol 335 (March 2012) discloses calculating information regarding oxygen saturation as functional information of a subject by using a plurality of absorption coefficient distributions corresponding to a plurality of wavelengths.

SUMMARY

Diagnostic performance by a photoacoustic device may be impaired when an error occurs in calculation of photoacoustic image data obtained by the photoacoustic device due to a calculation error or the like of a light fluence distribution, and a value that deviates from the true value in functional information of a subject is calculated.

Therefore, an object of the disclosure of the present specification is to improve accuracy of functional information of a subject in photoacoustic imaging.

Note that the object of the disclosure of the present specification is not limited to the above object, and it is possible to position, as one of other objects of the disclosure, obtaining an operation effect that is derived from configurations shown in DESCRIPTION OF THE EMBODIMENTS described later, and that cannot be obtained by a conventional technology.

An image processing device disclosed in the present specification includes a display control unit configured to display, on a display unit, an image obtained by visualizing functional information related to optical characteristics of a subject based on a photoacoustic signal obtained by receiving a photoacoustic wave generated in the subject by irradiating the subject with light, and a correction unit configured to correct the functional information of the image displayed on the display unit based on a first image value of the functional information of the image displayed on the display unit and a second image value of the functional information.

Further features of the present invention will become apparent from the following description of exemplary embodiments (with reference to the attached drawings).

According to the disclosure of the present specification, it is possible to improve accuracy of functional information of a subject in photoacoustic imaging.

DESCRIPTION OF THE EMBODIMENTS

Figure 1:
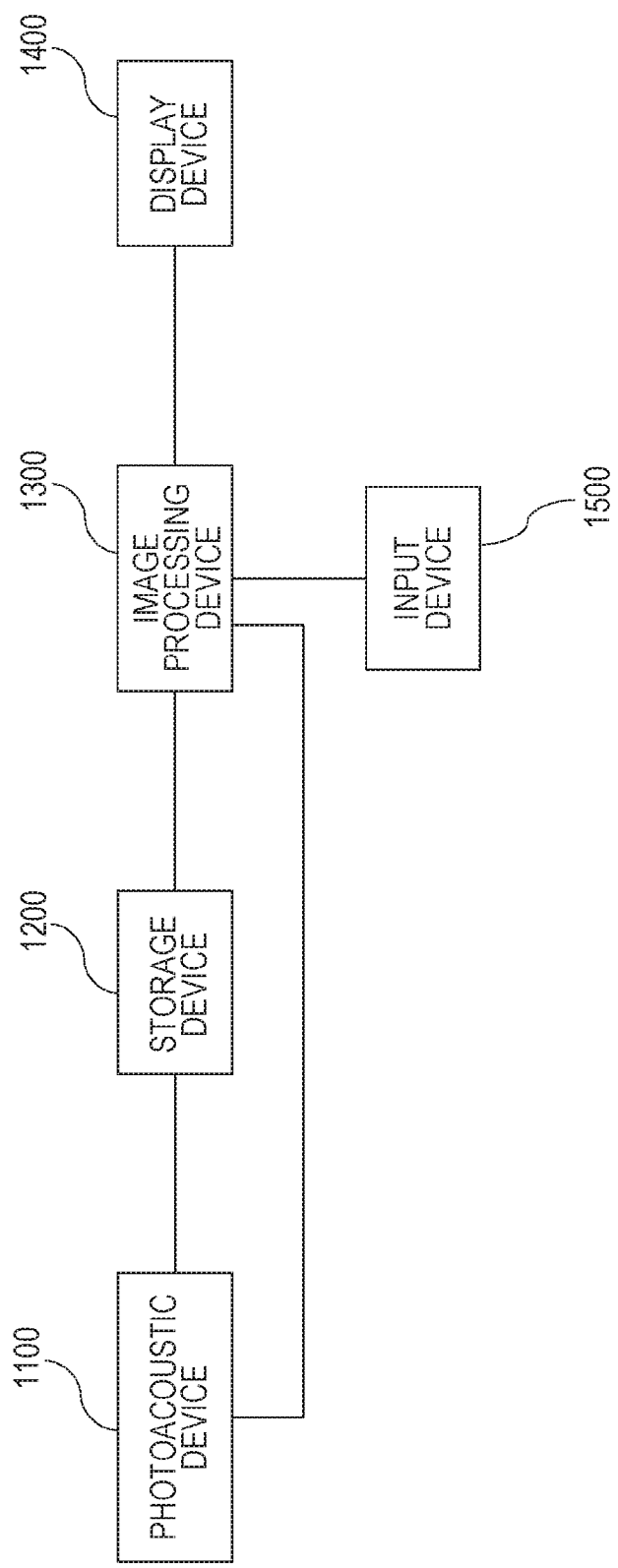
FIG. 1 is a block diagram illustrating an example of a configuration of a system according to a first embodiment.

Hereinafter, preferred embodiments of an image processing device disclosed in the present specification will be described with reference to the drawings. However, dimensions, materials, shapes, relative arrangements, and the like of components described below should be appropriately changed depending on a configuration of a device to which the invention is applied and various conditions. Therefore, the scope of the present invention is not intended to be limited to the following description.

A photoacoustic image obtained by a system according to the image processing device disclosed in the present specification reflects an absorption amount and an absorption rate of light energy. The photoacoustic image is an image representing a spatial distribution of at least one piece of subject information such as a generation sound pressure (initial sound pressure) of a photoacoustic wave, an optical absorption energy density, and an optical absorption coefficient. The photoacoustic image may be an image representing a two-dimensional spatial distribution, or may be an image representing a three-dimensional spatial distribution (volume data). Note that the photoacoustic image may be an image representing a two-dimensional spatial distribution in the depth direction from the subject surface or an image representing a three-dimensional spatial distribution in the depth direction from the subject surface.

In addition, the system according to the image processing device disclosed in the present specification can generate a functional image of a subject by using a plurality of photoacoustic images corresponding to a plurality of wavelengths. The functional image may be an image indicating information corresponding to the concentration of a substance constituting the subject, such as a glucose concentration, a collagen concentration, a melanin concentration, and a volume fraction of fat and water. The functional image may be an oxygen saturation image $SO_2(r)$ generated by using an absorption coefficient image $\mu_a^{\lambda_1}(r)$ based on a photoacoustic wave generated by irradiation of light having a first wavelength $\lambda_1$ and an absorption coefficient image $\mu_a^{\lambda_2}(r)$ based on a photoacoustic wave generated by irradiation of light having a second wavelength $\lambda_2$. For example, the system according to the present invention may generate the oxygen saturation image $SO_2(r)$ as the functional image according to Expression (1).

[Mathematical Formula 1]

$$SO_2(r) = \frac{\frac{\mu_a^{\lambda_2}(r)}{\mu_a^{\lambda_1}(r)} \cdot \varepsilon_{Hb}^{\lambda_1} - \varepsilon_{Hb}^{\lambda_2}}{(\varepsilon_{HbO}^{\lambda_2} - \varepsilon_{Hb}^{\lambda_2}) \frac{\mu_a^{\lambda_2}(r)}{\mu_a^{\lambda_1}(r)} (\varepsilon_{HbO}^{\lambda_1} - \varepsilon_{Hb}^{\lambda_1})} \quad \text{Expression (1)}$$

Here, $\varepsilon_{Hb}^{\lambda_1}$ indicates a molar absorption coefficient of deoxyhemoglobin [mm$^{-1}$ mol$^{-1}$] corresponding to the first wavelength $\lambda_1$, and $\varepsilon_{Hb}^{\lambda_2}$ indicates a molar absorption coefficient [mm$^{-1}$ mol$^{-1}$] of deoxyhemoglobin corresponding to the second wavelength $\lambda_2$. $\varepsilon_{HbO}^{\lambda_1}$ indicates a molar absorption coefficient [mm$^{-1}$ mol$^{-1}$] of oxyhemoglobin corresponding to the first wavelength $\lambda_1$, and $\varepsilon_{HbO}^{\lambda_2}$ indicates a molar absorption coefficient [mm$^{-1}$ mol$^{-1}$] of oxyhemoglobin corresponding to the second wavelength $\lambda_2$. r indicates a position.

Furthermore, the system according to the image processing device disclosed in the present specification may use, as the functional image, an image indicating a ratio between a first photoacoustic image based on a photoacoustic wave generated by irradiation of the light having the first wavelength $\lambda_1$ and a second photoacoustic image based on a photoacoustic wave generated by irradiation of the light having the second wavelength $\lambda_2$. That is, the system may use, as the functional image, an image based on the ratio between the first photoacoustic image based on the photoacoustic wave generated by irradiation of the light having the first wavelength $\lambda_1$ and the second photoacoustic image based on the photoacoustic wave generated by irradiation of the light having the second wavelength $\lambda_2$. Note that an image generated according to a modified expression of Expression (1) can also be expressed by the ratio between the first photoacoustic image and the second photoacoustic image, and thus it can be said that the image is an image based on the ratio between the first photoacoustic image and the second photoacoustic image (functional image).

Note that the functional image may be an image representing a two-dimensional spatial distribution in the depth direction from the subject surface or an image representing a three-dimensional spatial distribution in the depth direction from the subject surface.

First Embodiment

Hereinafter, a configuration of a system and an image processing method of the present embodiment will be described.

The system according to the present embodiment will be described with reference to FIG. 1. FIG. 1 is a block diagram illustrating an example of the configuration of the system according to the present embodiment. The system according to the present embodiment includes a photoacoustic device 1100, a storage device 1200, an image processing device 1300, a display device 1400, and an input device 1500. Transmission and reception of data between the devices may be performed by wire or wirelessly.

The photoacoustic device 1100 generates a photoacoustic image by imaging a subject, and outputs the photoacoustic image to the storage device 1200 or the image processing device 1300. The photoacoustic device 1100 acquires information on characteristic values each corresponding to one of a plurality of positions in the subject by using a reception signal obtained by receiving a photoacoustic wave generated by light irradiation. That is, the photoacoustic device 1100 acquires image data (photoacoustic image) obtained by visualizing functional information related to optical characteristics of the subject based on a photoacoustic signal obtained by receiving the photoacoustic wave generated in the subject by irradiating the subject with light.

The storage device 1200 may be a storage medium such as a read only memory (ROM), a magnetic disk, or a flash memory. Furthermore, the storage device 1200 may be a storage server via a network such as a picture archiving and communication system (PACS). That is, the storage device 1200 corresponds to an example of a storage unit.

The image processing device 1300 is a device that processes the photoacoustic image stored in the storage device 1200 and information such as incidental information of the photoacoustic image.

Units having an arithmetic function of the image processing device 1300 can be configured with a processor such as a central processing unit (CPU) and a graphics processing unit (GPU) or an arithmetic circuit such as a field programmable gate array (FPGA) chip. These units may be configured not only with a single processor or arithmetic circuit but also with a plurality of processors or arithmetic circuits.

A unit having a storage function of the image processing device 1300 can be configured with a non-transitory storage medium such as a ROM, a magnetic disk, or a flash memory. Furthermore, the unit having the storage function may be a volatile medium such as a random access memory (RAM). Note that a storage medium in which a program is stored is the non-transitory storage medium. Note that the unit having the storage function may be configured not only with a single storage medium but also with a plurality of storage media. That is, the unit having the storage function of the image processing device 1300 corresponds to an example of the storage unit.

A unit having a control function of the image processing device 1300 is configured with an arithmetic element such as a CPU. The unit having the control function controls the operation of each component of the system. The unit having the control function may control each component of the system in response to an instruction signal from various operations such as a start of measurement from the input unit. Furthermore, the unit having the control function may read out a program code stored in the storage unit and control the operation of each component of the system.

The display device 1400 is a display such as a liquid crystal display or an organic electro luminescence (EL) display. The display device 1400 may display an image or a graphical user interface (GUI) for operating the device.

As the input device 1500, an operation console can be employed that can be operated by a user and includes a mouse and a keyboard. Furthermore, the display device 1400 may be configured with a touch panel and used as the input device 1500.

Figure 2:
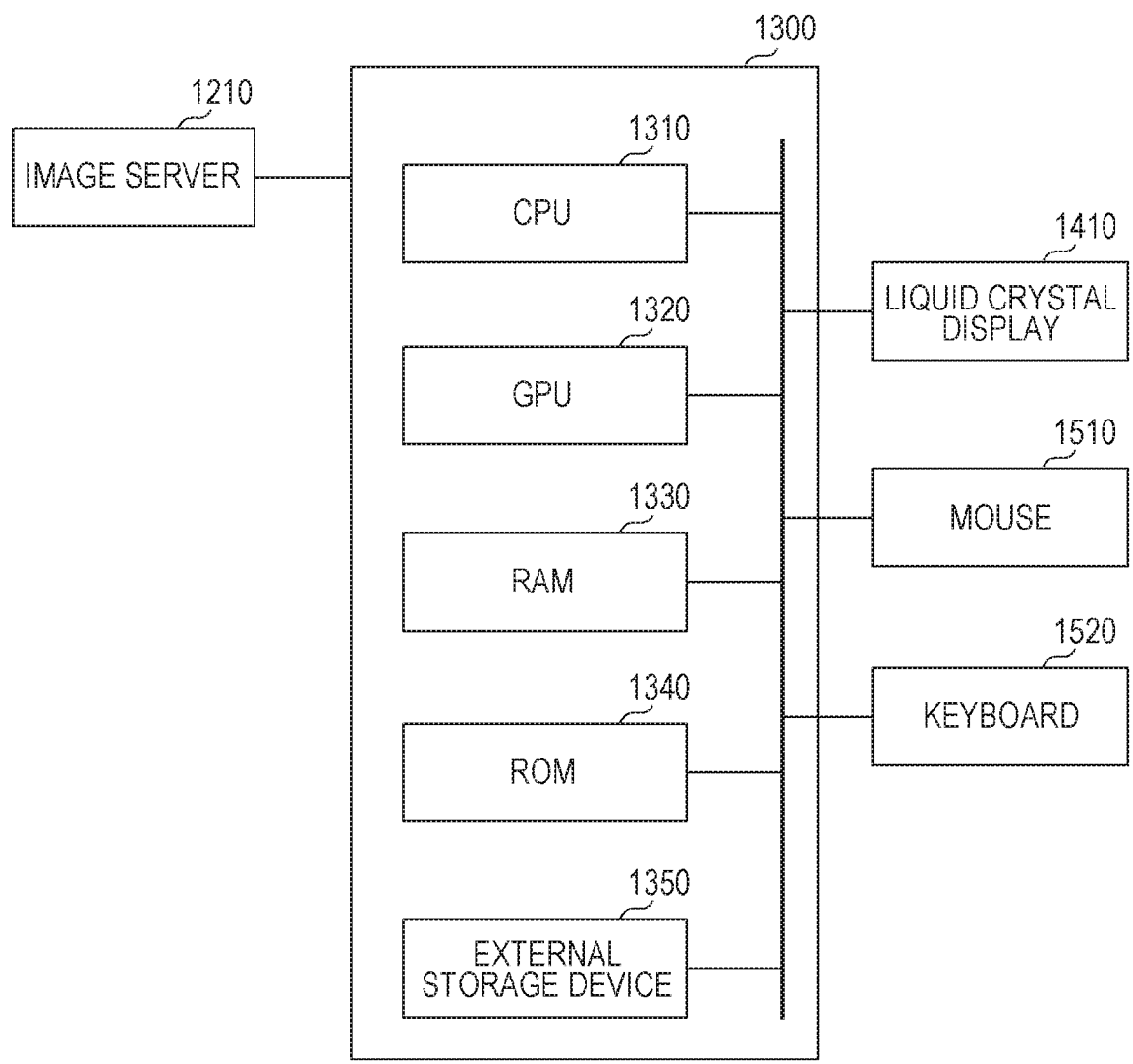
FIG. 2 is a block diagram illustrating an example of an image processing device according to the first embodiment and a peripheral configuration thereof.

FIG. 2 illustrates a specific configuration example of the system according to the present embodiment illustrated in FIG. 1. The image processing device 1300 includes a CPU 1310, a GPU 1320, a RAM 1330, a ROM 1340, and an external storage device 1350. A liquid crystal display 1410 as the display device 1400 is connected to the image processing device 1300. Furthermore, a mouse 1510 and a keyboard 1520 as the input device 1500 are connected. Furthermore, the image processing device 1300 is connected to an image server 1210 as the storage device 1200 such as a PACS. With this configuration, it is possible to store image data on the image server 1210 and to display, on the liquid crystal display 1410, the image data on the image server 1210.

Next, a configuration example of the device included in the system according to the present embodiment will be described.

Figure 3:
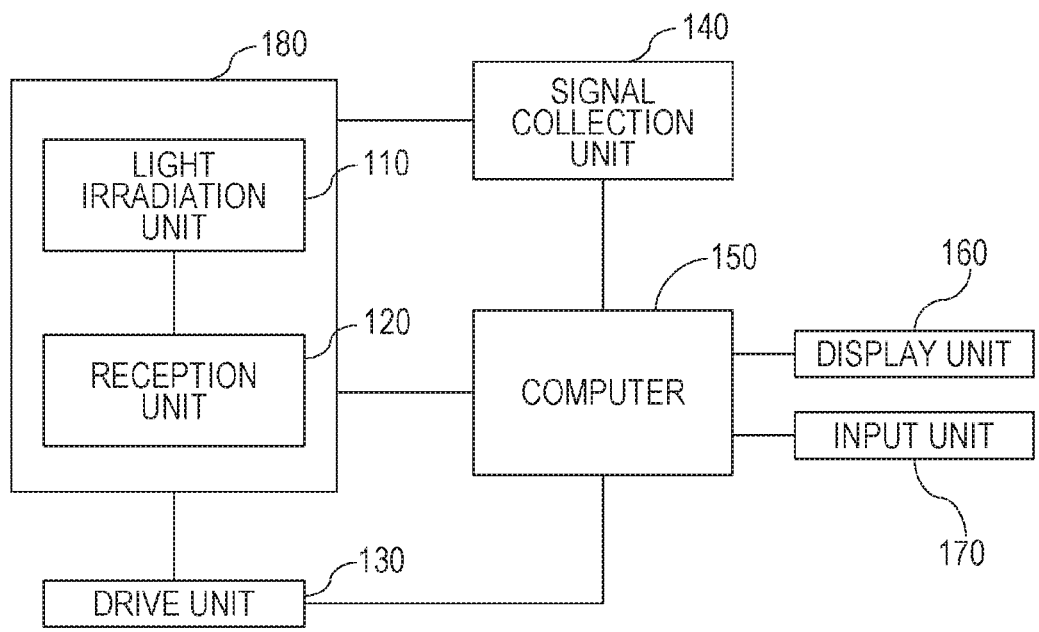
FIG. 3 is a block diagram illustrating an example of a detailed configuration of a photoacoustic device according to the first embodiment.

FIG. 3 is a schematic block diagram of the device included in the system according to the present embodiment.

Figure 4:
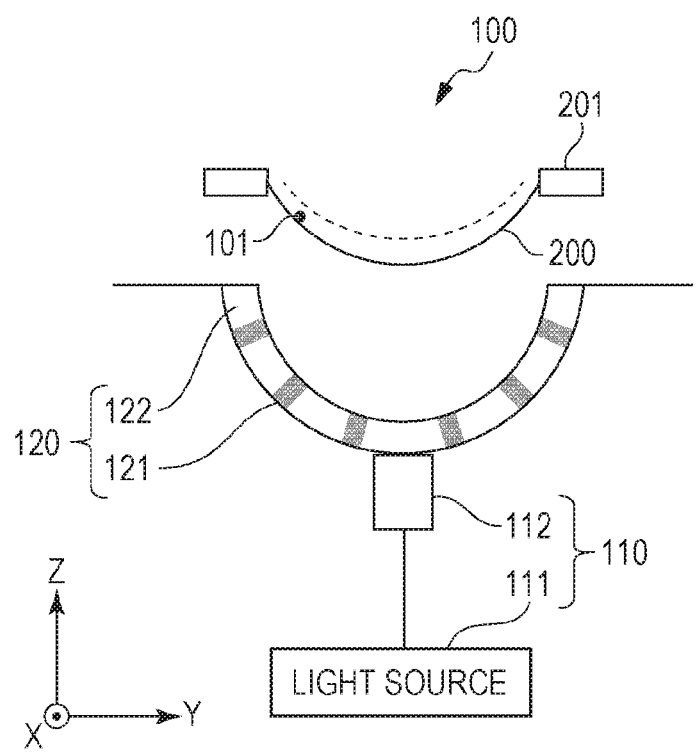
FIG. 4 is a schematic view illustrating an example of a probe according to the first embodiment.

The photoacoustic device 1100 according to the present embodiment includes a drive unit 130, a signal collection unit 140, a computer 150, and a probe 180. The probe 180 includes a light irradiation unit 110 and a reception unit 120. In addition, FIG. 4 is a schematic view of the probe 180 according to the present embodiment. A subject to be measured is a subject 100. The drive unit 130 drives the light irradiation unit 110 and the reception unit 120 to perform mechanical scanning. The light irradiation unit 110 irradiates the subject 100 with light, and an acoustic wave is generated in the subject 100. The acoustic wave generated by a photoacoustic effect due to light is also called a photoacoustic wave. The reception unit 120 outputs an electric signal (photoacoustic signal) as an analog signal by receiving the photoacoustic wave.

The signal collection unit 140 converts the analog signal output from the reception unit 120 into a digital signal, and outputs the digital signal to the computer 150. The computer 150 stores the digital signal output from the signal collection unit 140 as signal data derived from the photoacoustic wave.

The computer 150 generates a photoacoustic image by performing signal processing on the stored digital signal. Furthermore, the computer 150 performs image processing on the obtained photoacoustic image, and then outputs the photoacoustic image to a display unit 160. The display unit 160 displays an image based on the photoacoustic image. The displayed image is stored in the storage device 1200 such as a memory in the computer 150 or a data management system connected to a modality via a network based on a storage instruction from a user or the computer 150.

The computer 150 also performs drive control of the components included in the photoacoustic device 1100. In addition, the display unit 160 may display a GUI or the like in addition to the image generated by the computer 150. An input unit 170 is configured to allow a user to input information. The user can perform operations such as start and end of measurement and an instruction to store a created image by using the input unit 170.

Hereinafter, details of each component of the photoacoustic device 1100 according to the present embodiment will be described.

(Light Irradiation Unit 110)

The light irradiation unit 110 includes a light source 111 and an optical system 112. The light source 111 emits light, and the optical system 112 guides the light emitted from the light source 111 to the subject 100. Note that the light includes pulse light such as a so-called square wave and triangular wave.

The pulse width of the light emitted from the light source 111 may be 1 ns or more and 100 ns or less. Furthermore, the wavelength of the light may be in the range of about 400 nm to 1600 nm. When a blood vessel is imaged with high resolution, a wavelength at which absorption in the blood vessel is large (400 nm or more and 700 nm or less) may be used. When a deep part of a living body is imaged, light having a wavelength at which absorption in a background tissue (water, fat, or the like) of the living body is typically small (700 nm or more and 1100 nm or less) may be used.

As the light source 111, a laser or a light emitting diode can be used. In addition, when light having a plurality of wavelengths is used in measuring, a light source of which the wavelength can be changed may be used. Note that, when irradiating the subject with light having a plurality of wavelengths, it is also possible to prepare a plurality of light sources that generate light having wavelengths different from each other and irradiate the subject alternately from each of the light sources. When the plurality of light sources is used, the plurality of light sources is collectively expressed as the light source. Various lasers such as a solid-state laser, a gas laser, a dye laser, and a semiconductor laser can be used as the laser. For example, a pulse laser such as an Nd:YAG laser or an alexandrite laser may be used as the light source. Furthermore, a Ti:sa laser using the Nd:YAG laser light as excited light or an optical parametric oscillator (OPO) laser may be used as the light source. Furthermore, a flash lamp or a light emitting diode may be used as the light source 111. Furthermore, a microwave source may be used as the light source 111.

An optical element such as a lens, a mirror, and an optical fiber can be used for the optical system 112. In a case where a breast or the like is used as the subject 100, a light emission unit of the optical system 112 may be configured with a diffusion plate or the like that diffuses light in order to irradiate the subject 100 with pulse light having a wider beam diameter. On the other hand, in a photoacoustic microscope, in order to increase the resolution, the light emission unit of the optical system 112 may be configured with a lens or the like, and a beam may be focused to irradiate the subject 100.

Note that the light irradiation unit 110 may directly irradiate the subject 100 with light from the light source 111, without including the optical system 112.

(Reception Unit 120)

The reception unit 120 includes a transducer 121 and a supporting member 122. The transducer 121 outputs an electric signal by receiving an acoustic wave, and the supporting member 122 supports the transducer 121. Furthermore, the transducer 121 may be a transmission unit that transmits an acoustic wave. A transducer as a reception unit and a transducer as the transmission unit may be a single (common) transducer, or may be configured separately.

As a member constituting the transducer 121, a piezoelectric ceramic material represented by lead zirconate titanate (PZT), a polymer piezoelectric film material represented by polyvinylidene fluoride (PVDF), or the like can be used. Furthermore, an element other than a piezoelectric element may be used. For example, a capacitive transducer (capacitive micro-machined ultrasonic transducer (CMUT)), a transducer using a Fabry-Perot interferometer, or the like can be used. Note that any transducer may be employed as long as the transducer can output an electric signal by receiving an acoustic wave. In addition, a signal obtained by the transducer is a time resolved signal. That is, the amplitude of the signal obtained by the transducer represents a value based on a sound pressure received by the transducer at each time (for example, a value proportional to the sound pressure).

Frequency components constituting the photoacoustic wave is typically 100 KHz to 100 MHz, and a transducer that can detect these frequencies may be employed as the transducer 121.

The supporting member 122 may include a metal material having high mechanical strength. In order to make a large amount of irradiation light incident on the subject, the surface of the supporting member 122 on the side of the subject 100 may be subjected to mirror finishing or light scattering processing. In the present embodiment, the supporting member 122 has a hemispherical shell shape, and is configured to be able to support a plurality of the transducers 121 on the hemispherical shell. In this case, directional axes of the transducers 121 arranged on the supporting member 122 are gathered near the center of curvature of the hemisphere. As a result, when an image is formed by using signals output from the plurality of transducers 121, the image quality near the center of curvature becomes high. Note that the supporting member 122 may have any configuration as long as the supporting member 122 can support the transducer 121. The supporting member 122 may arrange a plurality of transducers in a plane or a curved surface such as a 1D array, a 1.5D array, a 1.75D array, and a 2D array. The plurality of transducers 121 correspond to a plurality of reception units.

Furthermore, the supporting member 122 may function as a container for storing an acoustic matching material. That is, the supporting member 122 may be a container for arranging the acoustic matching material between the transducers 121 and the subject 100.

Furthermore, the reception unit 120 may include an amplifier that amplifies time-series analog signals output from the transducers 121. In addition, the reception unit 120 may include an A/D converter that converts the time-series analog signals output from the transducers 121 into time-series digital signals. That is, the reception unit 120 may include the signal collection unit 140 described later.

Note that the transducers 121 may be ideally arranged to completely surround the subject 100 so that an acoustic wave can be detected from various angles. However, if the subject 100 is too large to arrange the transducers 121 to completely surround the subject 100, the transducers 121 may be arranged on the hemispherical supporting member 122 so that the subject 100 is for the most part surrounded by the transducers. Note that the arrangement and number of the transducers and the shape of the supporting member may be optimized according to the subject, and any type of the reception unit 120 can be employed in the present invention.

A space between the reception unit 120 and the subject 100 is filled with a medium that can propagate a photoacoustic wave. For this medium, a material is employed that can propagate the photoacoustic wave, has acoustic characteristics matched at the interface with the subject 100 and the transducers 121, and has as high a transmittance of the photoacoustic wave as possible. For example, water, ultrasonic gel, or the like can be employed as the medium.

FIG. 4 is a side view of the probe 180. The probe 180 according to the present embodiment includes the reception unit 120 in which the plurality of transducers 121 is three-dimensionally arranged on the hemispherical supporting member 122 having an opening. At the bottom of the supporting member 122, a light emission unit of the optical system 112 is arranged.

In the present embodiment, as illustrated in FIG. 4, the shape of the subject 100 is held by contacting with a holding unit 200.

A space between the reception unit 120 and the holding unit 200 is filled with a medium that can propagate the photoacoustic wave (acoustic matching material). For this medium, a material is employed that can propagate the photoacoustic wave, has acoustic characteristics matched at the interface with the subject 100 and the transducer 121, and has as high a transmittance as possible of the photoacoustic wave. For example, water, ultrasonic gel, or the like can be used as the medium.

The holding unit 200 as a holding unit is used to hold the shape of the subject 100 during measurement. By holding the subject 100 with the holding unit 200, it is possible to reduce the movement of the subject 100 and to keep the position of the subject 100 in the holding unit 200. As a material of the holding unit 200, resin material such as polycarbonate, polyethylene, or polyethylene terephthalate can be used. That is, it is preferable that the holding unit 200 includes a material having the hardness at which the holding unit 200 can hold the subject 100. Furthermore, the holding unit 200 may include a material that transmits light used for measurement. In addition, the holding unit 200 may include a material having the same impedance as that of the subject 100. When the subject 100 has a curved surface such as a breast, the holding unit 200 may be formed in a concave shape. In this case, the subject 100 can be inserted into a concave portion of the holding unit 200.

The holding unit 200 is attached to an attachment unit 201. The attachment unit 201 may be configured so that a plurality of types of the holding units 200 can be exchanged according to the size of the subject. For example, the attachment unit 201 may be configured so that the holding unit can be exchanged for a holding unit with a different radius of curvature or a different center of curvature.

Furthermore, the holding unit 200 may be provided with a tag in which information of the holding unit 200 is registered and a reading unit that reads the information registered in the tag. For example, information such as the radius of curvature, the center of curvature, the sound speed, and an identification ID of the holding unit 200 can be registered in the tag. The information registered in the tag is read out by the reading unit and transferred to the computer 150. In order to easily read the tag when the holding unit 200 is attached to the attachment unit 201, the attachment unit 201 may be provided with the reading unit. For example, the tag is a barcode, and the reading unit is a barcode reader.

(Drive Unit 130)

The drive unit 130 is a unit that changes the relative position between the subject 100 and the reception unit 120. The drive unit 130 includes a motor such as a stepping motor that generates a driving force, a driving mechanism that transmits the driving force, and a position sensor that detects position information of the reception unit 120. As the driving mechanism, a leading screw mechanism, a link mechanism, a gear mechanism, a hydraulic mechanism, or the like can be used. As the position sensor, a potentiometer or the like using an encoder, a variable resistor, a linear scale, a magnetic sensor, an infrared sensor, an ultrasonic sensor, or the like can be used.

Note that the drive unit 130 is not limited to a unit that changes the relative position between the subject 100 and the reception unit 120 in the XY direction (two-dimensionally), but may change the relative position one-dimensionally or three-dimensionally.

Regarding a moving path of the probe 180, scanning may be performed planarly in a spiral shape or in a line-and-space shape, or may be performed three-dimensionally by tilting the probe 180 along the body surface. Furthermore, the probe 180 may be moved such that the distance from the surface of the subject 100 is kept constant. At this time, the drive unit 130 may measure a moving amount of the probe 180 by monitoring the number of rotations of the motor, for example.

Note that the drive unit 130 may fix the reception unit 120 and move the subject 100 as long as the relative position between the subject 100 and the reception unit 120 can be changed. When the subject 100 is moved, a configuration can be considered in which the subject 100 is moved by moving the holding unit 200 that holds the subject 100. Furthermore, both the subject 100 and the reception unit 120 may be moved.

The drive unit 130 may move the relative position continuously or in a step-and-repeat manner. The drive unit 130 may be an electric stage that moves the relative position along a programmed locus or a manual stage.

Furthermore, in the present embodiment, the drive unit 130 drives the light irradiation unit 110 and the reception unit 120 at the same time to perform scanning. However, the drive unit 130 may drive only the light irradiation unit 110 or only the reception unit 120.

Note that, when the probe 180 is a handheld type probe provided with a grip portion, the photoacoustic device 1100 does not need to include the drive unit 130.

(Signal Collection Unit 140)

The signal collection unit 140 includes an amplifier that amplifies an electric signal that is an analog signal output from the transducer 121, and an A/D converter that converts the analog signal output from the amplifier into a digital signal. The digital signal output from the signal collection unit 140 is stored in the computer 150. The signal collection unit 140 is also called a data acquisition system (DAS). In the present specification, the electric signal is a concept including both the analog signal and the digital signal. Note that a light detection sensor such as a photodiode may detect light emission from the light irradiation unit 110, and the signal collection unit 140 may synchronize the detection result with a trigger, so that the above processing is started.

(Computer 150)

The computer 150 as an information processing device is configured with hardware similar to that of the image processing device 1300. That is, units having an arithmetic function of the computer 150 can be configured with a processor such as a CPU and a GPU or an arithmetic circuit such as an FPGA chip. These units may be configured not only with a single processor or arithmetic circuit but also with a plurality of processors or arithmetic circuits.

A unit having a storage function of the computer 150 may be a volatile medium such as a RAM. Note that a storage medium in which a program is stored is a non-transitory storage medium. Note that the unit having the storage function of the computer 150 may be configured not only with a single storage medium, but also with a plurality of storage media.

A unit having a control function of the computer 150 is configured with an arithmetic element such as a CPU. The unit having the control function of the computer 150 controls the operation of each component of the photoacoustic device. The unit having the control function of the computer 150 may control each component of the photoacoustic device in response to an instruction signal from various operations such as a start of measurement from the input unit 170. Furthermore, the unit having the control function of the computer 150 reads out a program code stored in the unit having the storage function, and controls the operation of each component of the photoacoustic device. That is, the computer 150 can function as a control device of the system according to the present embodiment.

Note that the computer 150 and the image processing device 1300 may be configured with the same hardware. One piece of hardware may have the functions of both the computer 150 and the image processing device 1300. That is, the computer 150 may have the function of the image processing device 1300. Furthermore, the image processing device 1300 may have the function of the computer 150 as the information processing device.

(Display Unit 160)

The display unit 160 is a display such as a liquid crystal display, an organic EL display, a field emission display (FED), a spectacle type display, and a head mounted display. Furthermore, the display unit 160 is a device that displays an image based on subject information and the like, a numerical value at a specific position, and the like obtained by the computer 150. In addition, the display unit 160 may display an image or a GUI for operating the device.

Note that the display unit 160 and the display device 1400 may be the same display. That is, one display may have the functions of both the display unit 160 and the display device 1400.

(Input Unit 170)

As the input unit 170, an operation console can be employed that can be operated by a user and includes a mouse and a keyboard. Furthermore, the display unit 160 may be configured with a touch panel and used as the input unit 170.

The input unit 170 may be capable of inputting information regarding a position, depth, and the like to be observed. As an input method, a numerical value may be input, or a slider bar may be operated to perform input. Furthermore, an image displayed on the display unit 160 may be updated according to the input information. As a result, a user can set appropriate parameters while checking an image generated by parameters determined by the user's own operation.

That is, one device may have both functions of the input unit 170 and the input device 1500.

(Subject 100)

The subject 100 does not constitute the system, but will be described below. The system according to the present embodiment can be used for the purpose of diagnosing a malignant tumor or a vascular disease of a human or an animal, monitoring progress of chemotherapy, and the like. Therefore, the subject 100 is assumed to be a subject part to be diagnosed such as a breast, each organ, a vascular network, a head, a neck, an abdomen, and a limb including a finger or toe of a living body, specifically, a human body or an animal. For example, if a human body is a subject to be measured, oxyhemoglobin, deoxyhemoglobin, a blood vessel rich in oxyhemoglobin or deoxyhemoglobin, or a new blood vessel formed in the vicinity of a tumor may be an optical absorber. Furthermore, a plaque of a carotid artery wall or the like may be the optical absorber. In addition, melanin, collagen, lipids, or the like contained in the skin or the like may be the optical absorber. Furthermore, a phantom imitating a living body may be used as the subject 100.

Note that each component of the photoacoustic device may be configured as a separate device, or may be configured as one integrated device. In addition, at least a part of the components of the photoacoustic device may be configured as one integrated device.

(Functional Information Marker 101)

A functional information marker 101 is a marker in which one or a plurality of pieces of information corresponding to the concentration of a substance constituting the subject, such as oxygen saturation, a glucose concentration, a collagen concentration, a melanin concentration, and a volume fraction of fat and water, is known. By imaging together the subject 100 and the functional information marker 101 with the photoacoustic device, it is possible to reduce a functional information error of the subject. Details will be described in the following (Display Correction Flow of Functional Information).

A type and a numerical value of functional information of the functional information marker 101 may be stored in the storage unit, or may be input by a user.

The functional information marker 101 may be provided to the holding unit 200 or the subject 100. Furthermore, in order not to reduce visibility when a photoacoustic image of the subject is interpreted, it is desirable that the functional information marker 101 is sufficiently small in size relative to the subject 100, and that image values of a photoacoustic image of the functional information marker 101, such as a generation sound pressure (initial sound pressure) of a photoacoustic wave, an optical absorption energy density, and an optical absorption coefficient, are also smaller than image values of the photoacoustic image of the subject 100. Furthermore, a plurality of the functional information markers 101 may be provided in an imaging range. A plurality of markers having the same type of functional information and the same numerical value of the functional information may be provided, or a plurality of markers having the same type of functional information and different numerical values of the functional information, or having different types of functional information may be provided.

Note that each device constituting the system according to the present embodiment may be configured with separate hardware, or all the devices may be configured with one piece of hardware.

That is, the function of the system according to the present embodiment may be configured with any hardware.

(Flow for Acquiring Photoacoustic Image)

Figure 5:
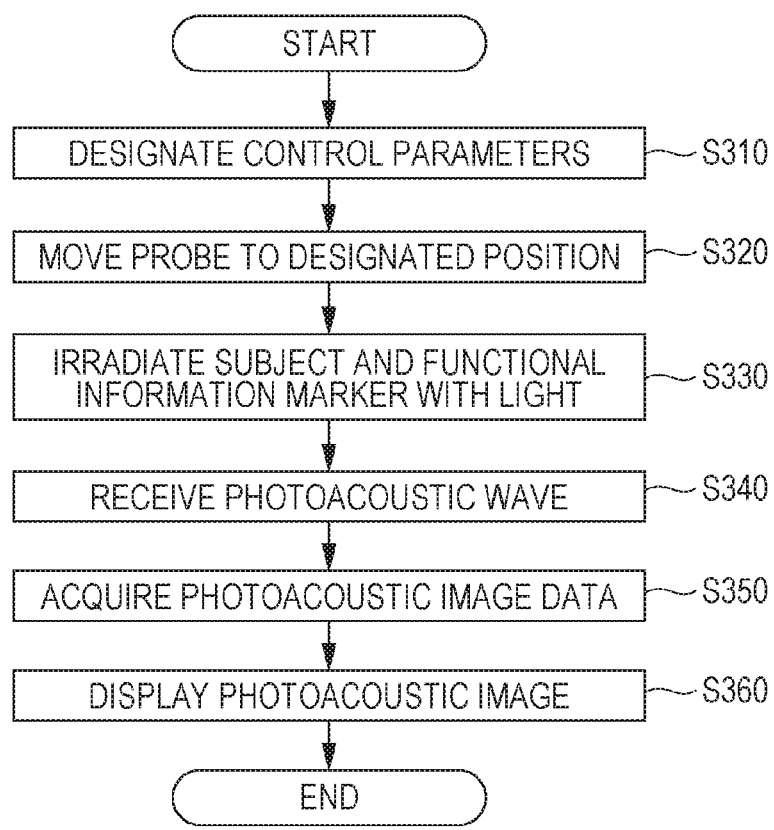
FIG. 5 is a flowchart illustrating an example of an image processing method according to the first embodiment.

Next, a method for acquiring a photoacoustic image according to the present embodiment will be described with reference to a flowchart illustrated in FIG. 5.

(S310: Designation of Control Parameter)

A user designates, by using the input unit 170, control parameters necessary for acquiring the subject information, such as an irradiation condition (repetition frequency, wavelength, and the like) of the light irradiation unit 110 and the position of the probe 180. The computer 150 sets the control parameters determined based on an instruction of the user.

(S320: Movement of Probe to Designated Position)

The computer 150 causes the drive unit 130 to move the probe 180 to a designated position based on the control parameters designated in step S301. When imaging at a plurality of positions is designated in step S310, the drive unit 130 first moves the probe 180 to a first designated position. Note that the drive unit 130 may move the probe 180 to a position programmed in advance when a measurement start instruction is issued.

(S330: Light Irradiation)

The light irradiation unit 110 irradiates the subject 100 and the functional information marker 101 with light based on the control parameters designated in S310.

The light generated from the light source 111 is applied to the subject 100 and the functional information marker 101 via the optical system 112 as pulse light. The pulse light is then absorbed inside the subject 100, and a photoacoustic wave is generated by a photoacoustic effect. The light irradiation unit 110 transmits a synchronization signal to the signal collection unit 140 together with the transmission of the pulse light.

(S340: Reception of Photoacoustic Wave)

Upon receiving the synchronization signal transmitted from the light irradiation unit 110, the signal collection unit 140 starts a signal collecting operation. That is, the signal collection unit 140 generates an amplified digital electric signal by amplifying and analog-to-digital (AD) converting an analog electric signal derived from an acoustic wave, which is output from the reception unit 120, and outputs the digital electric signal to the computer 150. The computer 150 stores the signal transmitted from the signal collection unit 140 in the storage unit. When imaging at a plurality of scanning positions is designated in step S301, steps S320 to S340 are repeatedly executed at the designated scanning positions, and irradiation of pulse light and generation of a digital signal derived from an acoustic wave are repeated. Note that the computer 150 may acquire and store, with light emission as a trigger, position information of the reception unit 120 at the time of the light emission based on output from the position sensor of the drive unit 130.

(S350: Acquisition of Photoacoustic Image Data)

The computer 150 as an image acquisition unit acquires photoacoustic image data as volume data based on signal data stored in the storage unit, and stores the photoacoustic image data in the storage unit. At this time, the computer 150 may acquire the photoacoustic image data based on the control parameters such as the position of the probe 180 in addition to the signal data.

As a reconstruction algorithm for converting signal data into volume data as a spatial distribution, an analytical reconstruction method such as a back projection method in the time domain or a back projection method in the Fourier domain, or a model-based method (iterative operation method) can be employed. For example, the back projection method in the time domain includes a universal back-projection (UBP), a filtered back-projection (FBP), and a phasing addition (delay-and-sum).

Furthermore, the computer 150 may calculate a light fluence distribution of the light applied to the subject 100 inside the subject 100, and acquire absorption coefficient distribution information by dividing an initial sound pressure distribution by the light fluence distribution. In this case, the absorption coefficient distribution information may be acquired as the photoacoustic image data. The computer 150 can calculate a spatial distribution of a light fluence inside the subject 100 by a method of numerically solving a transport equation and a diffusion equation indicating a behavior of light energy in a medium that absorbs and scatters light. As the numerically solving method, a finite element method, a difference method, a Monte Carlo method, or the like can be employed. For example, the computer 150 may calculate the spatial distribution of the light fluence inside the subject 100 by solving a light diffusion equation shown in Expression (2).

[Mathematical Formula 2]

$$\frac{1}{c}\frac{\partial}{\partial t}\Phi(r, t) = -\mu_a \Phi(r, t) + \nabla \cdot (D \nabla \Phi(r, t)) + S(r, t) \quad \text{Expression (2)}$$

Here, D indicates a diffusion coefficient, $\mu a$ indicates an absorption coefficient, S indicates an incident intensity of irradiation light, φ indicates a light fluence to reach, r indicates a position, and t indicates a time.

Furthermore, the processing of S330 and S340 may be executed by using light having a plurality of wavelengths, and in this processing, the computer 150 may acquire absorption coefficient distribution information corresponding to light having one of the plurality of wavelengths. Then, the computer 150 may acquire, as functional information, spatial distribution information of the concentration of a substance constituting the subject 100 based on the absorption coefficient distribution information corresponding to the light having one of the plurality of wavelengths.

Note that the computer 150 as an information processing device that is a device different from the modality may execute the image processing method according to the present embodiment. In this case, the computer 150 reads out image data generated by the modality in advance from the storage unit such as a PACS to acquire the image data, and applies, to the image data, the image processing method according to the present embodiment. As described above, the image processing method according to the present embodiment can also be applied to image data generated in advance.

(S360: Photoacoustic Image Display)

The computer 150 as a display control unit displays the photoacoustic image data obtained in S350 on the display unit 160. Note that, in addition to displaying the image data of the subject information as an image, the computer 150 may display a numerical value of the subject information at a specific position of the image.

(Display Correction Flow of Functional information)

Figure 6:
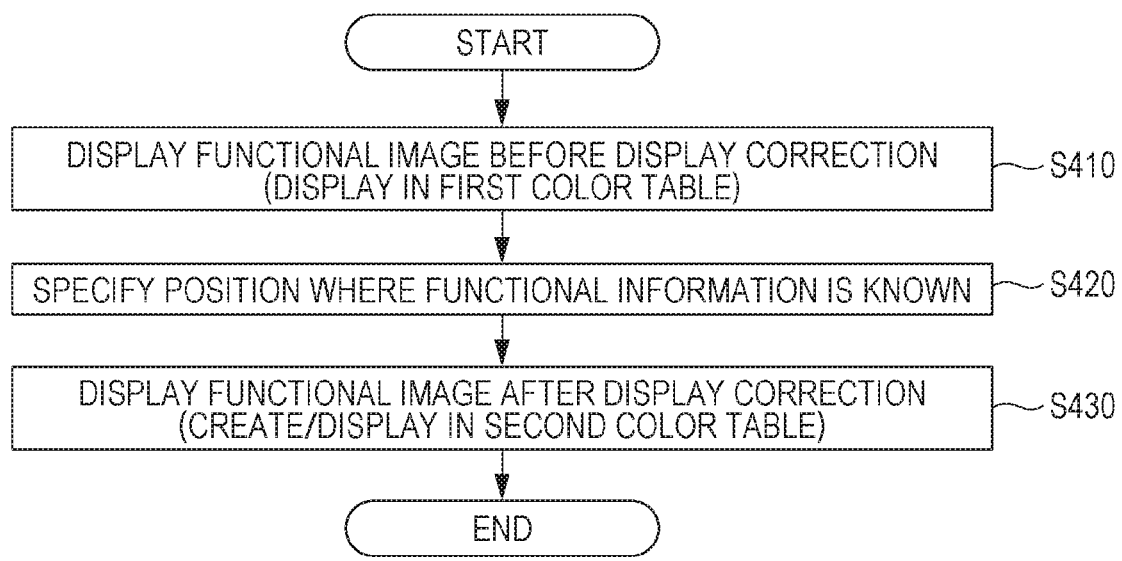
FIG. 6 is a flowchart illustrating an example of a method for correcting display of a functional image according to the first embodiment.

A value deviating from the true value in the functional information may be calculated due to a measurement error of an amount of light applied to the subject or an error in the calculation of the light fluence distribution described above. In this processing, by imaging together the subject 100 and the functional information marker 101 by the photoacoustic device, it is possible to reduce a functional information error of the subject. Here, this processing will be described in detail with reference to a flowchart illustrated in FIG. 6.

(S410: Display of Functional Image before Display Correction)

Figure 7:
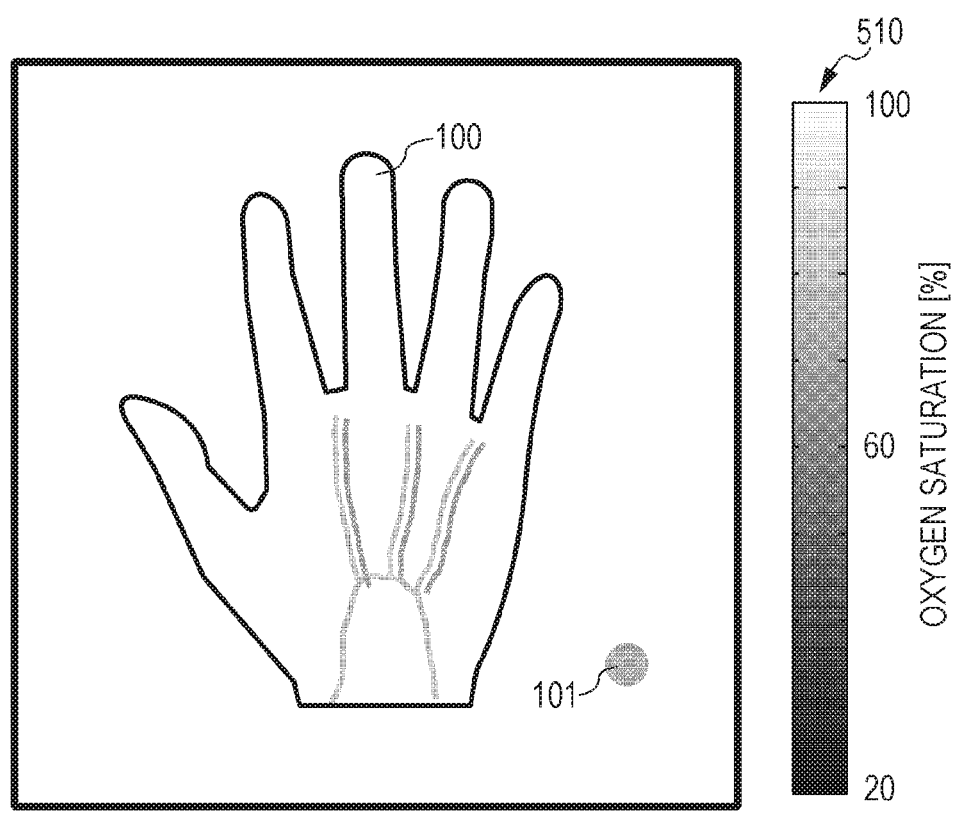
FIG. 7 is a view illustrating an example of display of a functional image according to the first embodiment.

The computer 150 generates, as a functional image, an oxygen saturation image by using Expression (1) from the absorption coefficient distribution information generated in S350. Furthermore, the computer 150 displays the obtained functional image on the display unit 160. A color table indicating a relationship between an image value and a display color of the functional image uses an initial value (first color table) stored in the storage unit, and a color bar 510 is displayed on the GUI as illustrated in FIG. 7. Note that the functional image may be displayed in parallel with the photoacoustic image displayed in S360, or may be displayed in a superimposed manner. At this time, at least one of hue, brightness, and saturation may be assigned to the image value of the functional image, and the remaining parameters of hue, brightness, and saturation may be assigned to an image value of the photoacoustic image so that the functional image and the photoacoustic image may be superimposed and displayed. For example, an image may be displayed in which hue and saturation are assigned to an image value of a spectral image and brightness is assigned to the image value of the photoacoustic image.

(S420: Specification of Position Where Functional Information Is Known)

A user specifies the position of the functional information marker 101 in the functional image displayed in S410. In the specification of the position of the functional information marker 101, the position may be designated by the user using a cursor from the input unit 170, or specified by the user designating a coordinate value. When the position of the functional information marker 101 is fixed, the position may be read from the storage unit. That is, the computer 150 accepts designation of a position where a numerical value of the functional information is known by performing an operation input for the image displayed on the display unit or by reading position information stored in the storage unit. In addition, when a plurality of the functional information markers 101 is provided, designation of a plurality of positions is accepted.

(S430: Display of Functional Image after Display Correction (Creation/Display in Second Color Table))

From the position of the functional information marker 101 specified in S420, the computer 150 reads an image value of the functional information marker 101 on the functional image, and creates a second color table for correcting the display of the functional information based on the image value.

A display correction amount of an image value of the functional information is determined from a difference value between the known numerical value of the functional information of the functional information marker 101 stored in the storage unit and the image value of the functional information marker 101 on the functional image, and the correction is performed. That is, the computer 150 corresponds to an example of a correction unit that corrects the functional information of the image displayed on the display unit based on the image value of the functional information of the image displayed on the display unit and the known image value of the functional information.

Figure 8A:
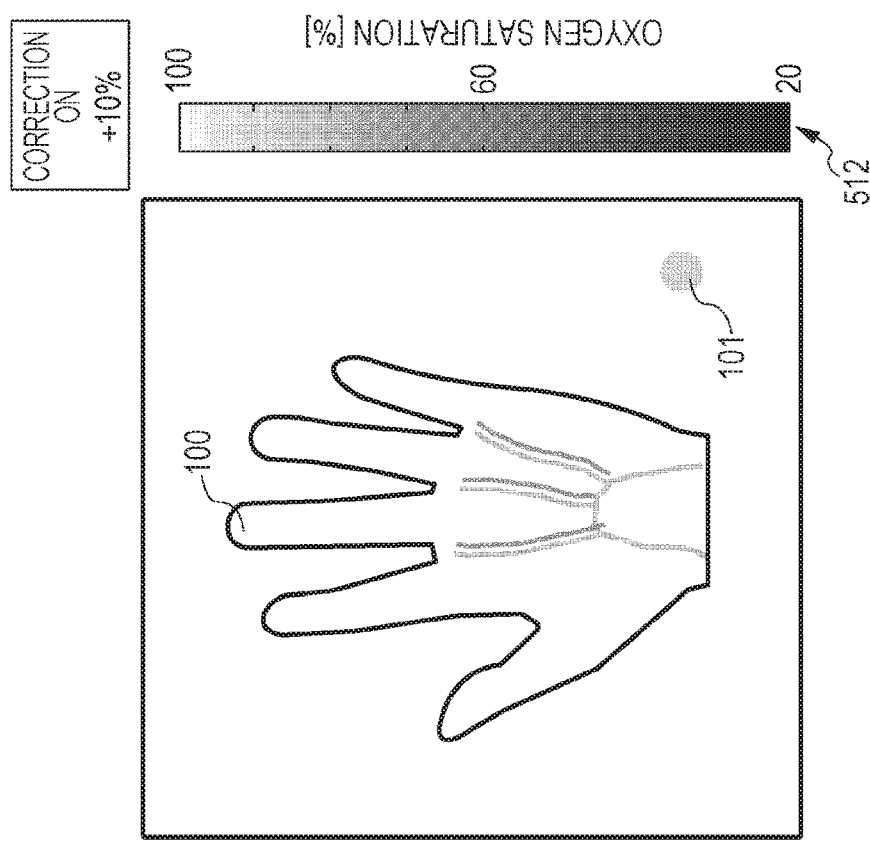
FIGS. 8A and 8B are views each illustrating an example of the method for correcting display of the functional image according to the first embodiment.

Specifically, for example, based on the display correction amount, correspondence of the image value of the functional image to the display color is corrected as illustrated in FIG. 8A, and a color bar 511 is displayed.

Figure 8B:
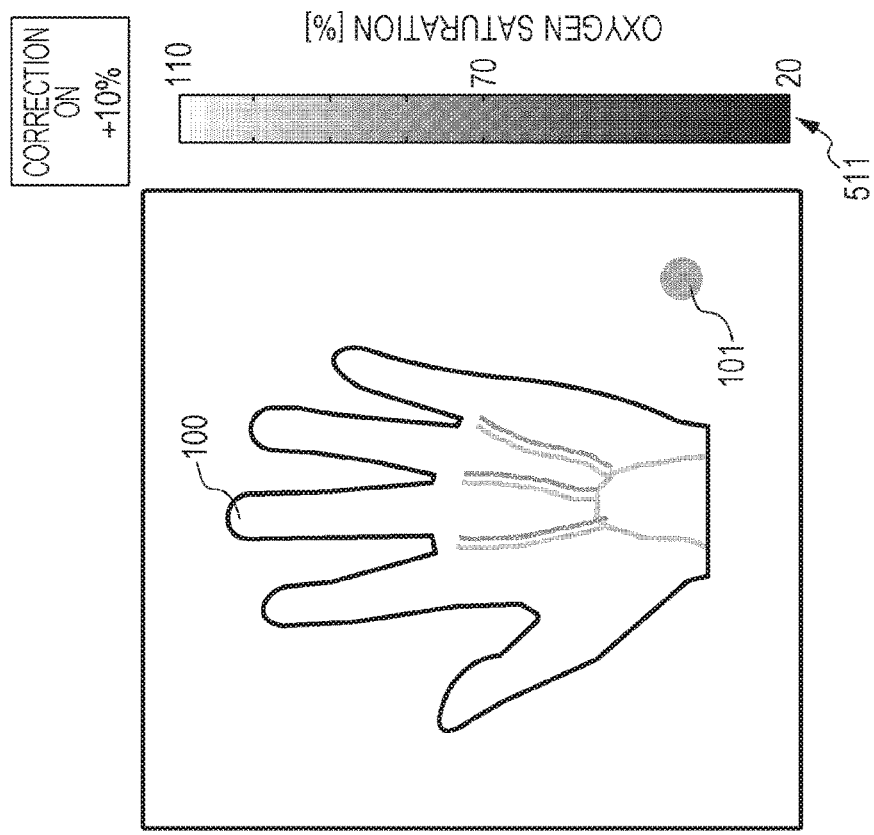

Alternatively, as illustrated in FIG. 8B, the display color for the image value of the functional image may be changed, and a color bar 512 may be displayed. That is, one of the color assigned to the image value of the functional information and a range of the image value of the functional information assigned to the color is corrected. At this time, the display unit 160 may display a message indicating that the display correction is being performed, or may display the display correction amount. Furthermore, a configuration may be employed in which the image value of the functional information of the functional information marker 101 can be input by a user using the input unit 170. In addition, a warning may be displayed on the display unit 160 when the display correction amount exceeds a certain threshold or is equal to or more than the threshold. Furthermore, although the color bar is displayed in the present embodiment, a table showing a relationship between the range of the image value of the functional information and the assigned color may be used, for example. That is, a display mode is not limited to the above mode as long as information indicating the relationship between the image value and the color of the functional information is displayed.

When a plurality of the functional information markers 101 is provided, differences between image values of the functional information markers 101 at a plurality of positions on the functional image are calculated, and the display correction amount of the image value of the functional information is determined. As the display correction amount of the image value of the functional information, an average value of the differences at the plurality of positions is calculated. However, the display correction amount is not limited to the average value, but may be any value as long as the value is calculated based on the differences between the plurality of positions. For example, the maximum value, the minimum value, or the median value may be used. Furthermore, the display correction amount may be changed in the functional image based on the differences between the plurality of positions.

Note that, in the present embodiment, the determination of the display correction amount of the image value of the functional information from the difference between the known value of the functional information of the functional information marker 101 and the image value of the functional information marker 101 on the functional image has been described. However, the display correction amount may be determined from a calculation value based on the known value of the functional information of the functional information marker 101 and the image value of the functional information marker 101 on the functional image, such as a ratio or a difference ratio, as well as the difference.

As described above, the processing in the system according to the present embodiment is performed.

According to the above configuration, even when a value deviating from the true value in the functional information of the subject is calculated, accuracy can be improved by performing the correction based on the position where the functional information is known. In addition, a user designates a position where reliability of the functional information is high, and corrects the functional information based on the position, so that highly accurate correction can be performed.

Second Embodiment

Next, processing in a second embodiment will be described. In the first embodiment, the correction is performed based on the numerical value of the functional information of the functional information marker 101. However, in the second embodiment, the display correction amount is calculated by using a specific position in the subject 100 as the position where the numerical value of the functional information is known, without using the functional information marker 101. Note that a configuration of a photoacoustic device according to the present embodiment and a flow for acquiring a photoacoustic image are similar to those in the first embodiment, and thus a detailed description thereof will be omitted.

(Display Correction Flow of Functional Information)

Figure 9:
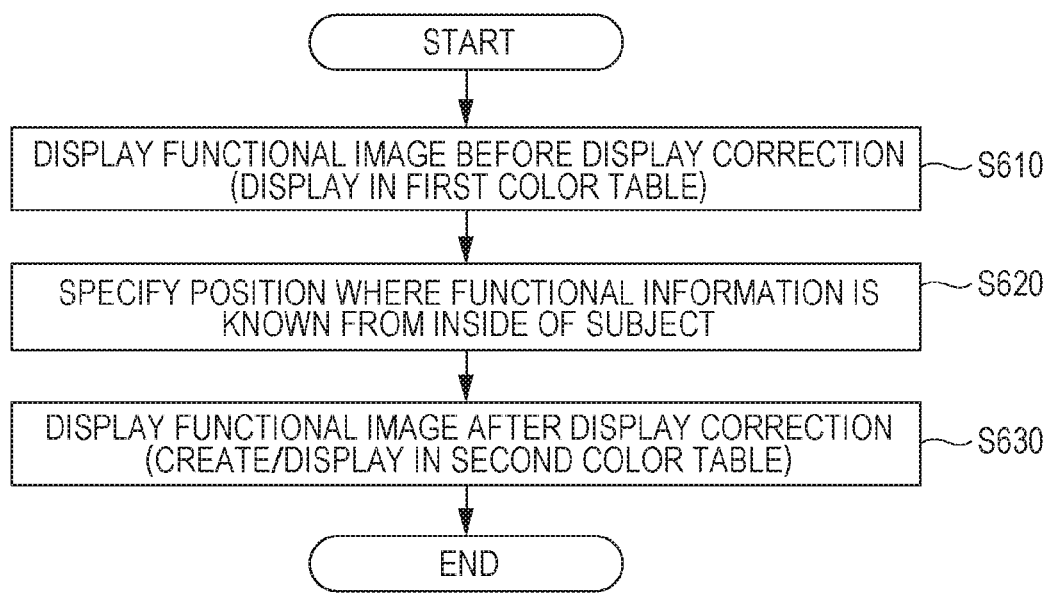
FIG. 9 is a flowchart illustrating an example of a method for correcting display of a functional image according to a second embodiment.

Next, each step of a display correction flow of functional information according to the present embodiment will be described with reference to FIG. 9. Step S610 is similar to step S410 of the first embodiment, and thus a description thereof will be omitted.

(S620: Specification of Position Where Numerical Value of Functional Information Is Known from Inside of Subject)

In the functional image displayed in S610, a user specifies a position in the subject 100 where a numerical value of the functional information is known. Here, the position in the subject 100 where a numerical value of the functional information is known is desirably a position in the subject where a numerical value of the functional information is small, such as an artery or a vein. When the photoacoustic image is captured by using a contrast agent whose image value is known, a region where the contrast agent flows may be designated as the position in the subject 100 where a numerical value of the functional information is known. For example, the region where the contrast agent flows indicates a blood vessel. Note that the position is not limited to the above.

The position in the subject 100 where a numerical value of the functional information is known may be designated by the user using a cursor from the input unit 170, or by the user designating a coordinate value. In addition, when the position in the subject 100 where a numerical value of the functional information is known can be specified in advance, the specified position may be read from the storage unit. Furthermore, as the position in the subject 100 where a numerical value of the functional information is known, a plurality of positions may be designated. In addition, when the position in the subject 100 where a numerical value of the functional information is known is fixed, the position may be read from the storage unit. Furthermore, when a blood vessel or the like is designated, a section including the blood vessel may be continuously designated. When the section including the blood vessel is continuously designated, the position where a numerical value of the functional information is known may be designated by designating a starting point and an end point and automatically performing a trace.

(S630: Display of Functional Image after Display Correction (Creation/Display in Second Color Table))

From the position in the subject 100 where a numerical value of the functional information is known, which is specified in S620, an image value at the position in the subject 100 where a numerical value of the functional information is known on the functional image is read. Based on this image value, a second color table for correcting the display of the functional information is created.

A method for creating the second color table is similar to that in step S430 of the first embodiment, and thus a description thereof will be omitted. When a section including the blood vessel is continuously designated as the position in the subject 100 where an image value of the functional image is known, differences at a plurality of positions on the blood vessel on the functional image are calculated, and the display correction amount of an image value of the functional information is determined. As the display correction amount of the image value of the functional information, an average value of the differences at the plurality of positions is calculated. However, the display correction amount is not limited to the average value, and may be any value as long as the value is calculated based on the differences between the plurality of positions. For example, the maximum value, the minimum value, or the median value may be used. Furthermore, the display correction amount may be changed in the functional image based on the differences between the plurality of positions.

According to the above configuration, even when a value deviating from the true value in the functional information of the subject is calculated, accuracy can be improved by performing the correction based on the position where the functional information is known. In addition, a user designates a position where reliability of the functional information is high, and corrects the functional information based on the position, so that highly accurate correction can be performed.

Other Embodiments

The present invention is also realized by executing the following processing. That is, the present invention is realized by executing the processing in which software (program) that implements the functions of the above-described embodiments is supplied to a system or a device via a network or various storage media, and a computer (or a CPU, an MPU, or the like) of the system or the device reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-064694, filed Mar. 28, 2019, which is hereby incorporated by reference herein in its entirety.

What is claimed is:

1. An image processing device comprising:
a memory storing a program; and
one or more processors which, by executing the program, function as:
a display control unit configured to display, on a display unit, an image obtained by visualizing functional information related to optical characteristics of a subject based on a photoacoustic signal obtained by receiving a photoacoustic wave generated in the subject by irradiating the subject with light;
a correction unit configured to correct the functional information of the image displayed on the display unit based on a first image value of the functional information of the image displayed on the display unit and a second image value of the functional information; and
an acceptance unit configured to accepts designation of a position where a numerical value of the functional information is known by an operation input to the image displayed on the display unit,
wherein a position corresponding to the second image value of the functional information is identified based on a position of a marker imaged together with the subject.

2. The image processing device according to claim 1, wherein the correction unit corrects one of a color assigned to the first image value of the functional information and a range of the first image value of the functional information assigned to the color.

3. The image processing device according to claim 1, wherein the correction unit corrects the functional information of the image displayed on the display unit based on a difference between the first image value of the functional information of the image displayed on the display unit and the second image value of the functional information.

4. The image processing device according to claim 1, wherein the acceptance unit is configured to accept designation of a position in the image displayed on the display unit, wherein the correction unit corrects the functional information of the image displayed on the display unit based on the first image value of the functional information at the designated position of the image and the second image value of the functional information at the designated position.

5. The image processing device according to claim 1, wherein, when positions of a plurality of the markers are designated, the correction unit corrects the functional information of the image displayed on the display unit based on at least one value of a plurality of differences between image values of the plurality of markers displayed on the display unit and a known image value of the marker.

6. The image processing device according to claim 1, wherein, when positions of a plurality of the markers are designated, the correction unit corrects the functional information of the image displayed on the display unit based on a difference between at least one of the image values of the plurality of markers displayed on the display unit and a known image value of the marker.

7. The image processing device according to claim 6, wherein the position where a numerical value of the functional information is known is a position in the subject where a change in the functional information is small.

8. The image processing device according to claim 7, wherein the acceptance unit accepts the designation of the position where a numerical value of the functional information is known by tracing a section between a start point and an end point input to the image displayed on the display unit.

9. The image processing device according to claim 7, wherein the position where a change in the functional information is small corresponds to at least one of an artery, a vein, and a region where a contrast agent flows in the subject.

10. The image processing device according to claim 1, wherein the display control unit further displays, on the display unit, information indicating a relationship between the first image value and a color of the functional information.

11. The image processing device according to claim 10, wherein the correction unit corrects the information indicating the relationship between the first image value and the color of the functional information based on the first image value of the functional information of the image displayed on the display unit and the second image value of the functional information.

12. The image processing device according to claim 1, wherein the display control unit further displays, on the display unit, a correction amount in the correction by the correction unit.

13. The image processing device according to claim 1, wherein the display control unit displays a warning when a correction amount in the correction by the correction unit is equal to or larger than a threshold.

14. An image processing method comprising:
displaying, on a display unit, an image obtained by visualizing functional information related to optical characteristics of a subject based on a photoacoustic signal obtained by receiving a photoacoustic wave generated in the subject by irradiating the subject with light;
correcting the functional information of the image displayed on the display unit based on a first image value of the functional information of the image displayed on the display unit and a second image value of the functional information; and
accept designation of a position where a numerical value of the functional information is known by an operation input to the image displayed on the display unit,
wherein a position corresponding to the second image value of the functional information is identified based on a position of a marker imaged together with the subject.

15. The image processing method according to claim 14, further comprising accepting designation of a position in the image displayed on the display unit, wherein, in the correcting, the functional information of the image displayed on the display unit is corrected based on a first image value of the functional information at the designated position of the image and a second image value of the functional information at the designated position.

16. A non-transitory computer-readable medium storing a program for causing a computer to execute control of each unit of an image processing device comprising:

a display control unit configured to display, on a display unit, an image obtained by visualizing functional information related to optical characteristics of a subject based on a photoacoustic signal obtained by receiving a photoacoustic wave generated in the subject by irradiating the subject with light;

and a correction unit configured to correct the functional information of the image displayed on the display unit based on a first image value of the functional information of the image displayed on the display unit and a second image value of the functional information; and accept designation of a position where a numerical value of the functional information is known by an operation input to the image displayed on the display unit, wherein a position corresponding to the second image value of the functional information is identified based on a position of a marker imaged together with the subject.

* * * * *